United States Patent
Leahy et al.

[19]

[11] Patent Number: 5,981,949
[45] Date of Patent: Nov. 9, 1999

[54] LOCATING DEFECTS IN SOLID MATERIAL

[75] Inventors: Darin J. Leahy, Stoneham; Maxwell M. Chi, Bedford; Jonathan M. Mooney, Winchester; Michael N. Alexander, Lexington, all of Mass.

[73] Assignee: The United States of America as represented by the Secretary of the Air Force, Washington, D.C.

[21] Appl. No.: 08/963,156

[22] Filed: Nov. 3, 1997

Related U.S. Application Data

[63] Continuation of application No. 08/588,490, Jan. 18, 1996, abandoned.

[51] Int. Cl.$^6$ .................................................... G01N 21/00
[52] U.S. Cl. ........................................ 250/332; 250/341.4
[58] Field of Search .................................. 250/330, 332, 250/341.4

[56] References Cited

U.S. PATENT DOCUMENTS 3,767,304  10/1973  Keenan et al. ...................... 250/341.4
5,077,475  12/1991  Moriya et al. .......................... 250/330
5,126,569   6/1992  Carlson ................................. 250/341.4
5,512,749   4/1996  Iddan et al. ............................ 250/332
5,528,368   6/1996  Lewis et al. ........................ 250/339.02

*Primary Examiner*—Edward P. Westin
*Assistant Examiner*—Richard Hanig
*Attorney, Agent, or Firm*—Thomas C. Stover

[57] ABSTRACT

The invention provides method and apparatus for fast, accurate, and nondestructive imaging of defects and determining defect densities in solid materials including a semiconductor wafer. A wafer is illuminated on one side by an infrared (IR) source and a camera is placed on the other side of the wafer, to detect IR radiation that is transmitted through such wafer. The inventive method employs an imaging camera, e.g. a focal plane array camera, to image the so illuminated wafer. The wafer material must be substantially transparent in the camera bandwidth but can contain defects that absorb or scatter radiation in such bandwidth. Camera filters are used, for example, to select specific wavelengths or bands of wavelengths, to detect and image precipitates, subsurface defects, residual damage from polishing and other defects.

16 Claims, 5 Drawing Sheets

DETERMINATION OF TRANSMITTANCE

FOR THE FIRST INCIDENT WAVELENGTH : RECORD THE SIGNAL LEVEL FROM THE CAMERA AT EACH PIXEL FOR THE WAFER IN FOCUS, FOR THE WAFER DEFOCUSSED, AND FOR THE WAFER OUT OF THE FIELD OF VIEW (1)

PERFORM BACKGROUND CORRECTION BY SUBTRACTING THE DEFOCUSSED SIGNAL FROM THE FOCUSSED SIGNAL AT EACH PIXEL. (2)

MEASURE $T$ THE AVERAGE TRANSMITTANCE THROUGH THE WAFER AS A FUNCTION OF INCIDENT WAVELENGTH USEING A SPECTROMETER (3)

FIND THE SIGNAL STRENGTH AT EACH PIXEL FOR THE WAFER OUT OF VIEW. CORRELATE THIS WITH 100 PERCENT TRANSMITTANCE (4)

FIND THE AVERAGE SIGNAL STRENGTH OVER ALL PIXELS FOR THE CORRECTED IMAGE FROM STEP 2. CORRELATE THIS WITH $T$ MEASURED IN STEP 3 (5)

INTERPOLATE LINEARLY THE PIXEL-BY-PIXEL SIGNAL IN THE CORRECTED IMAGE BETWEEN $T$ AND 100 PERCENT TRANSMITTANCE (6)

CREATE A FILE CONTAINING TRANSMITTANCE AT EACH PIXEL FOR THE FIRST INCIDENT WAVELENGTH (7)

REPEAT STEP 1-7 FOR THE SECOND INCIDENT WAVELENGTH (8)-(14)

DETERMINATION OF ABSORPTION AND EL2

FROM THE RESULTS OF STEPS 7 AND 14, CALCULATE ABSORPTION COEFFICIENT AT EACH PIXEL FOR EACH WAVELENGTH (15)

FROM THE ABSORPTION COFFICIENTS AND KNOWN PHOTOIONIZATION CROSS SECTIONS AT EACH WAVELENGTH, CALCULATE THE EL2 CONCENTRATION AND FERMI FILL FACTOR AT EACH PIXEL (16)

FIG. 6

LOCATING DEFECTS IN SOLID MATERIAL

This application is a continuation of application Ser. No. 08/588,490, filed Jan. 18, 1996, now abandoned.

STATEMENT OF GOVERNMENT INTEREST

The invention described herein may be manufactured and used by or for the Government for governmental purposes without the payment of any royalty thereon.

FIELD OF THE INVENTION

This invention relates to locating defects in solid material, particularly infrared transparent material.

BACKGROUND OF THE INVENTION

In the manufacture of semiconductor and in particular semi-insulating materials, e.g. in wafer form, there is a need for non-destructive testing thereof for defects in the material before relatively expensive electronic devices are built therefrom. These defects include dislocations and (in gallium arsenide, GaAs) EL2 defects. Clustering of defects, even of beneficial ones like EL2 (which makes GaAs semi-insulating) is undesirable. And as indicated above, useable electronic devices require high quality wafer material, which includes high uniformity across such material.

Infrared absorption has become a valuable technique for mapping the EL2 defect concentration in semi-insulating (SI) GaAs substrates. Two different methods are used. The first method, whole wafer mapping, is performed by illuminating the wafer with a lamp and photographing an image on the wafer's opposite side with, e.g. a camera having infrared sensitive film. This method is slow because it requires film processing. Although post-processing of the film image can be converted to quantitative maps of EL2, calibration of the film and light source is necessary, resulting in further delays and possible loss of image fidelity.

Another type of whole wafer mapping is performed by illuminating the wafer with a lamp and obtaining an image on the wafer's opposite side with a vidicon camera. This type of whole wafer mapping provides only qualitative data because the vidicon camera is neither sensitive nor uniform enough to provide truly quantitative images.

The second method is to use lenses to focus the light to a spot on the wafer about 1 mm in diameter and measure the transmission of light through the wafer at successive (1 mm wide) points, by moving the spot across the wafer or vice versa. Such spot scanning method provides a point-by-point EL2 concentration map, but typically requires about two hours to set up and scan each wafer.

For examples of spot scanning patents, see U.S. Pat. No. 5,126,569 to Carlson (1992) and U.S. Pat. No. 4,578,584 to Baumann (1986), which references are incorporated herein by reference.

For another example of spot scanning in the prior art see an Article by D. C. Look, et al. *A new technique for whole-wafer etch-pit density mapping in GaAs*, "J.Appl. Phys." 65 (3), 1375, Feb. 1, 1989, which Article is incorporated herein by reference. Also the spot scanning method can leave significant blanks in the image obtained, e.g. where the defect density varies rapidly within each spot.

Thus, there is need and market for a solid material defect mapping system that overcomes the above prior art shortcomings. There has now been discovered a fast, accurate, and non-destructive means of imaging defects and determining defect densities in solid materials. The method of the invention is highly suitable for obtaining accurate images and maps of concentration of defects, e.g. in whole semiconductor wafers or in either large or small portions of such wafers.

SUMMARY OF THE INVENTION

Broadly the present invention provides a method for locating defects and/or nonuniformities in a solid material that is otherwise substantially transparent to infrared (IR) light. Such method includes, a) placing an IR imaging camera before a source of IR radiation and spaced therefrom, b) placing the material between the camera and such source, c) activating the source to emit IR light through the material to the camera so that the camera obtains an image of the material and its defects, d) processing the image and e) outputting the image in a desired form.

The invention also provides an apparatus for locating defects and/or nonuniformities in a solid material that is otherwise substantially transparent to infrared (IR) light. The apparatus includes, a) a source of IR radiation, b) an IR imaging camera mounted before such source and spaced therefrom, c) means for placing the material between the camera and the source and d) means for activating the source to transmit IR light through the material to the camera, which obtains an image of the material and its defects. Also means are provided for processing and outputting such image in a desired form.

By "nonuniformities" as used herein, is meant nonuniform distribution of the atomic or molecular composition of solid material, (eg. a wafer) or of its components, its additives, or densities thereof or of other defects therein and/or of a coating thereon.

BRIEF DESCRIPTION OF THE DRAWINGS

The invention will become more apparent from the following detailed specification and drawings in which.

FIG. 6 is a flow diagram for calibration of an imaging system embodying the present invention.

DESCRIPTION OF PREFERRED EMBODIMENTS

Figure 2:
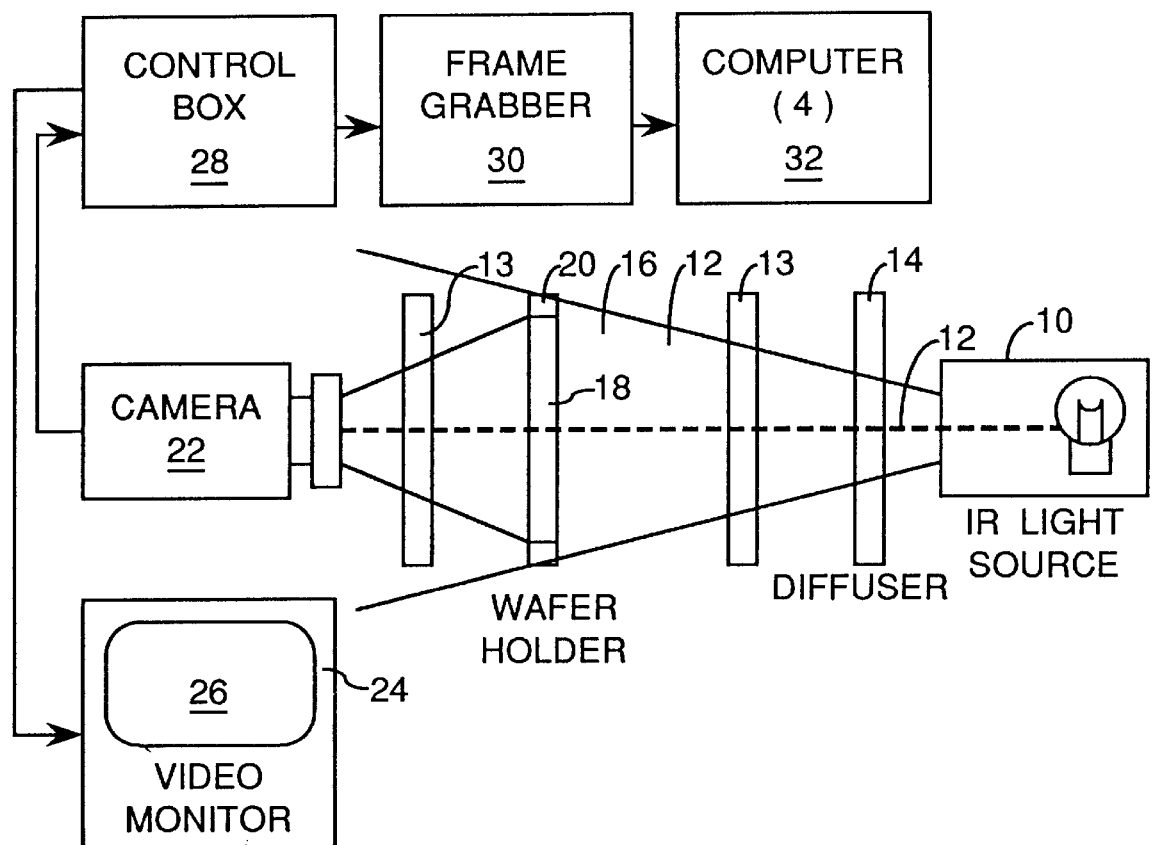
FIG. 2 is a schematic block diagram showing an apparatus embodying the present invention.

As illustrated in FIG. 2, a beam of light is used to illuminate an entire wafer. That is, an IR light source 10 projects a beam 12 through a beam diffuser 14, which diffuses such beam and illuminates an IR transparent wafer 18 in holder 20, as shown in FIG. 2. A diffuser is employed, if needed or desired, per the invention, to provide more uniform IR light distribution on the wafer from the light source 10. Also one or more light filters 13 can be employed for IR wavelength selection, if desired, as indicated in FIG. 2, and a filter may be added, if desired, to improve the signal to noise ratio.

A wafer mapping camera, e.g. a staring focal plane array infrared camera 22, positioned behind the illuminated wafer 18, focuses on and images the entire wafer 18 or a portion thereof, as shown in FIG. 2.

The camera 22 is connected to at least one output device such as a video monitor 24 for displaying the camera-obtained, wafer image on screen 26, as indicated in FIG. 2.

The control box 28 controls the functions of the camera 22, including transmitting the image obtained to the video monitor 24 and also to transmit such obtained image to a frame grabber 30, which converts such image to, e.g. a 12-bit digitized format and transmits such format to computer 32 for storage and analysis thereof.

The obtained image is thus processed per the invention, by one or more of the steps of transmitting it, converting it to a digitized format and transferring the digitized format to a computer, eg. for storage and analysis thereof Other image process steps are as noted below.

Thus the method of the invention uses a large area staring focal plane array infrared camera and can image a whole wafer or a large area of the wafer in about 10 seconds. Alternatively, employing suitable lenses for magnification, a small area of the wafer can be imaged and mapped with high spatial resolution. As noted above, the obtained image is digitized, e.g. at a 12-bit level and transferred to a computer (e.g. a microcomputer) for analysis. The total time, including digital image processing, is typically under two minutes. The resolution of the prior art system is 3500 points, on, e.g. a 4 inch diameter wafer. This compares with 80,000 points or more for the camera 22 employed in acquiring the data of FIGS. 3–5. Cameras having more than 1,000,000 pixels are commercially available and can be used in the method of the present invention.

The above digitized data can be extensively analyzed in the above computer to determine, e.g. wafer optical properties, wafer defect densities and wafer uniformity and can also be used by wafer manufacturers for process control. Again, such data collection process takes place in under two minutes. The processing of the above (image) data includes the steps of recording the signal strength at each of the camera pixels and converting the transmission values to defect densities, variations in chemical composition or other relevant parameters. Also a calibration procedure is employed, e.g. per FIG. 6 hereof, that requires two or more images be obtained; the wafer out of the system and the wafer in the system but out of focus. This method provides an accurate calibration for transmission of the in-focus wafer that, among other things, can remove errors due to non-uniform illumination of such wafer.

Figure 1:
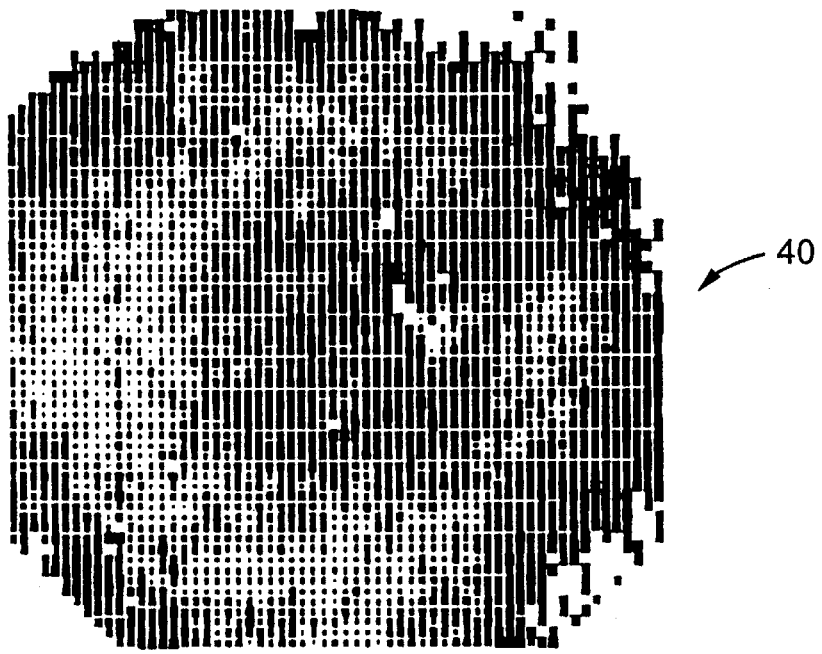
FIG. 1 is a wafer image obtained by a method of the prior art.
Figure 3:
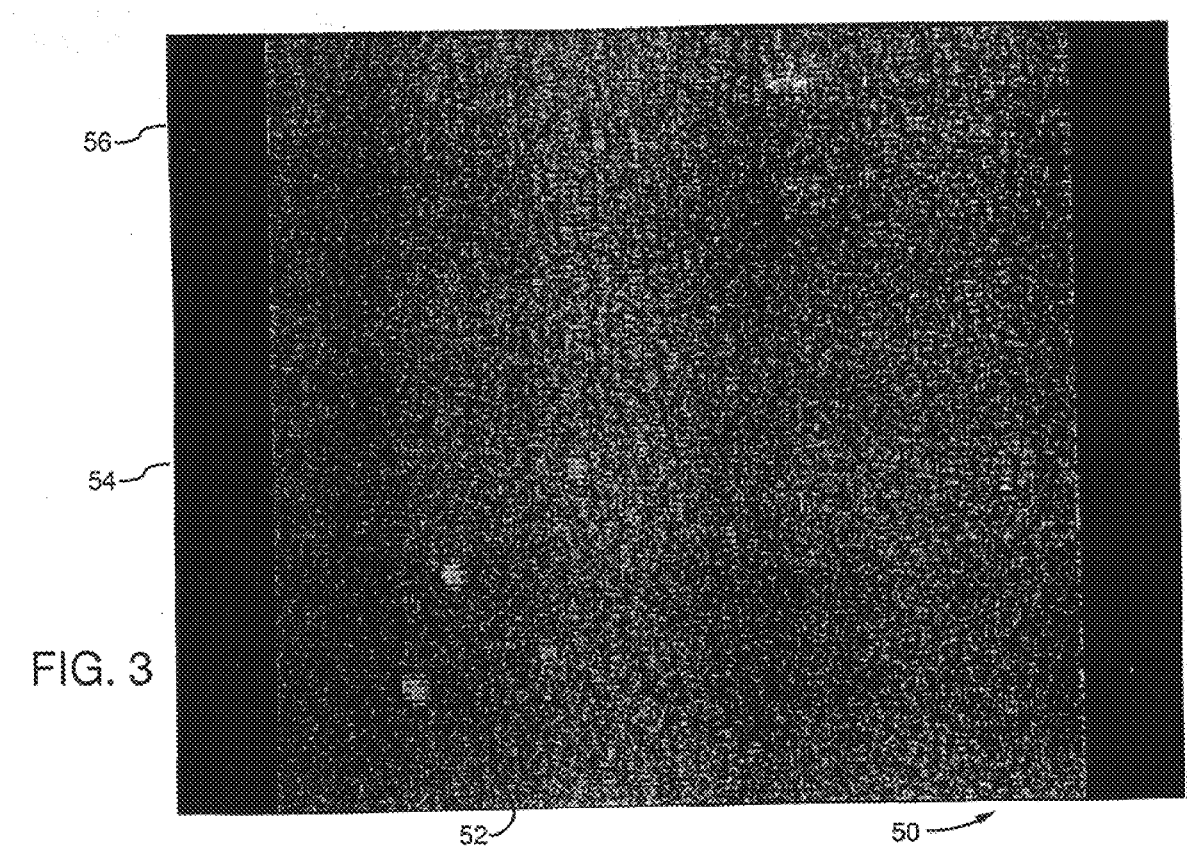
FIGS. 3, 4 and 5 are images taken of wafers or portions thereof by the imaging system of the present invention

The advance of wafer mapping per the method and apparatus of the present invention is indicated by comparing the results of an image obtained by the prior art spot scanning method, as shown in FIG. 1 with the image obtained by the wafer mapping of the present invention, e.g. as shown in FIG. 3. That is, in FIG. 1 the image is in the form of an unrefined grid with many blank spaces that can conceal wafer defects and other non-uniformities. However in FIG. 3, a detailed refined image of a wafer shows the optical properties with higher resolution.

Figure 4:
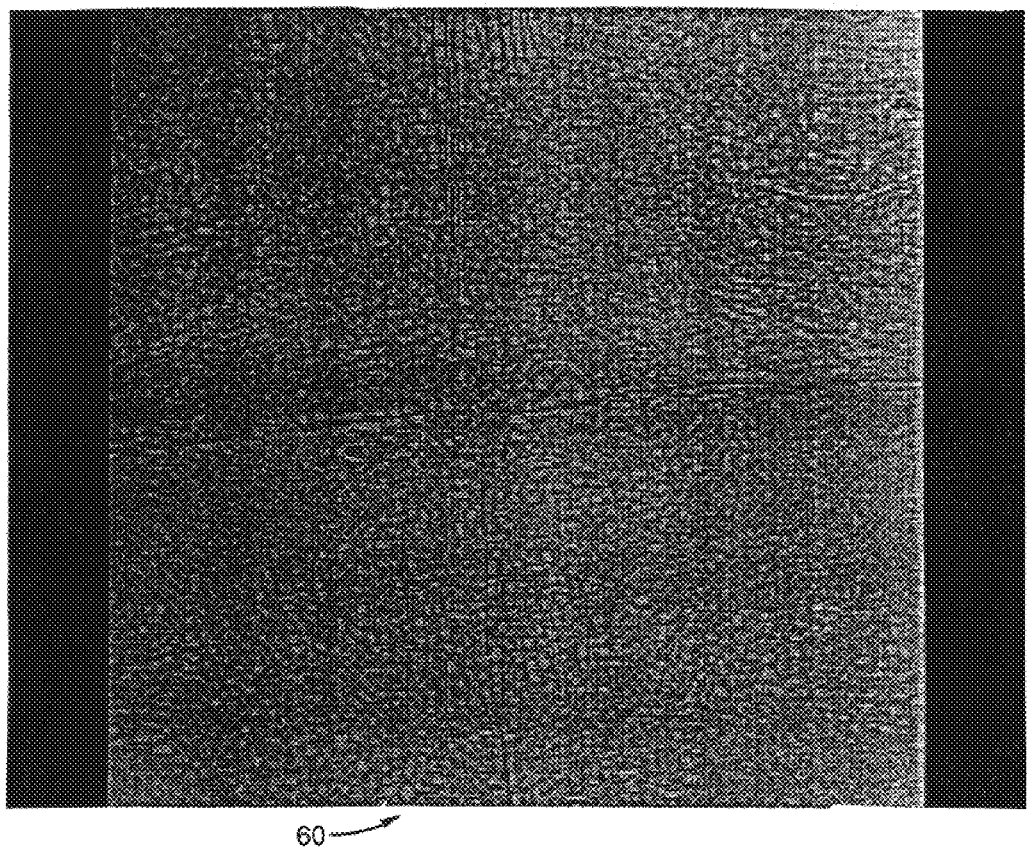

Further the wafer 60 imaged in FIG. 4 hereof, per the mapping system of the present invention, is shown in high clarity to have nearly uniform defect distribution. Accordingly such wafer can provide high quality substrates for a number of electronic devices, minimizing rejects.

The wafers shown in FIGS. 1, 3, and 4 are substantially of gallium arsenide (GaAs). However other types of wafers are clearly imaged by the mapping process of the present invention, including wafers of silicon (Si) and of indium phosphide (InP).

Figure 5:
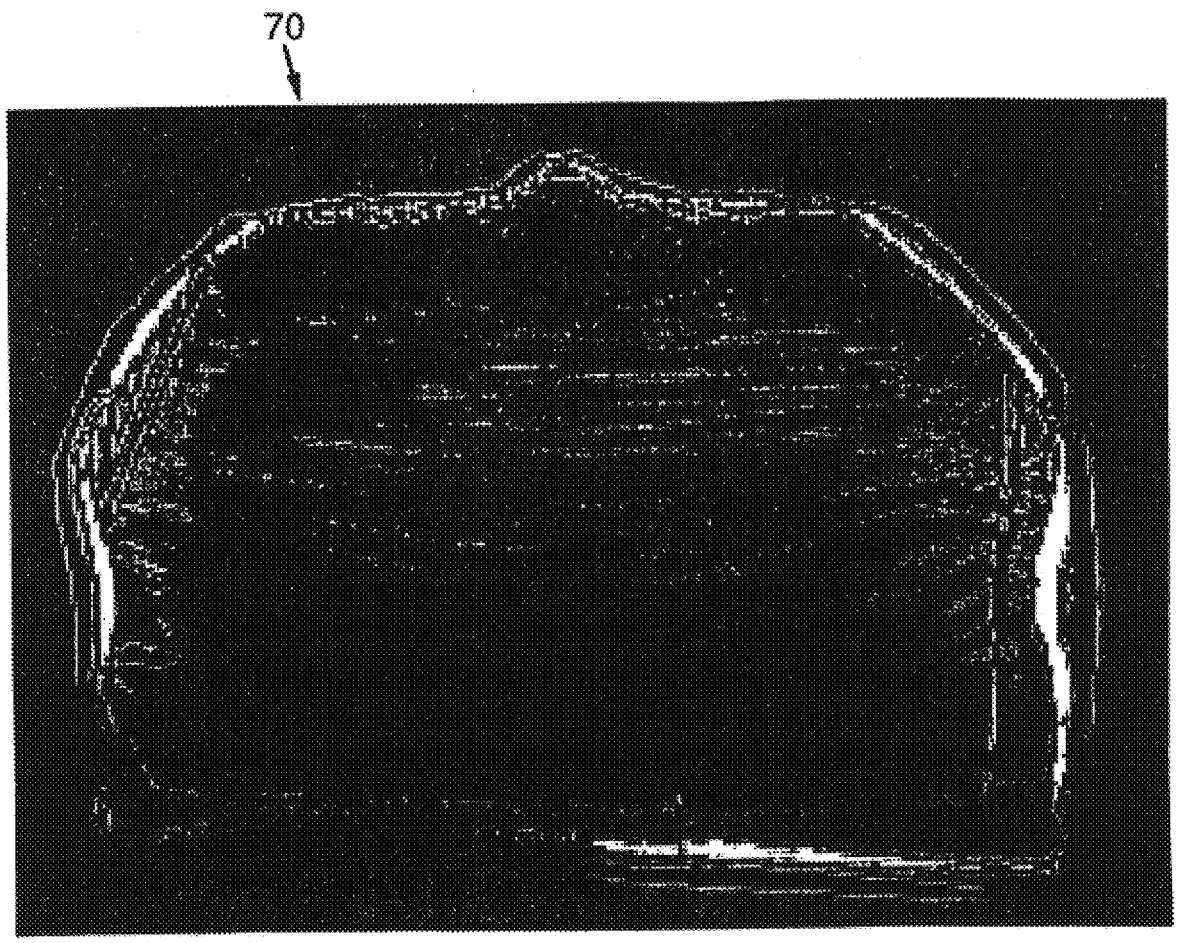

Thus FIG. 5 shows an infrared image of a wafer of Sn doped InP (in this case a wafer cut parallel to the crystal growth direction) imaged by the mapping system of the present invention. In the image of FIG. 5 can be seen a cross-section of the wafer in which striations therein are caused by fluctuations in growth conditions within the growing crystal or wafer 70. Nonuniformities near the wafer edges, probably due to crystal facetting, are also evident.

The method and apparatus of the present invention preferably employs a staring focal plane array camera to image large areas of solid material with both high spatial resolution and pixel to pixel uniformity, which is not possible with current state-of-the-art methods. The method overcomes the limitations of the two methods described earlier. With the present invention, accurate and detailed images of defect concentrations in large areas of solid materials can be obtained quickly and nondestructively.

As noted the preferred camera employed in the mapping system of the invention, is a staring focal plane array camera, e.g. one having a platinum-silicide (PtSi) focal plane array, as disclosed in U.S. Pat. No. 3,902,066 (1975), which patent is incorporated herein by reference. Such camera is able to image the entire wafer at once. Also the camera resolution, uniformity and linearity are such that the transmission can be determined, at tens of thousands or hundreds of thousands of individual points over a large diameter wafer. Any infrared camera can be used in the system of the invention provided it has the sensitivity and detector-to-detector uniformity, to measure non-uniformities and other defects in the wafer, to provide an accurate transmission map thereof From the transmission values and using standard calculations, the EL2 density of such wafer can be determined at each point. Once the camera is set up and the calibration performed, the data collection takes, e.g. about 10 seconds per wafer.

As noted above, a preferred embodiment of the invention employs a platinum silicide (PtSi) staring focal plane array camera to image a semiconductor or insulator material. As before, a wafer of such material is illuminated on its reverse side by a uniform IR source. Such camera rapidly images and processes, e.g. 80,000 points, with imaging over the entire wafer. Filters or other wavelength or band selection devices (such as a prism, a monochrometer or an interferometer) are used to select specific IR wavelengths or bands of wavelengths, to detect and image a wafer with precipitates, subsurface defects, residual damage from polishing or other defects. Also magnification means permit a small area of the wafer to be viewed and examined.

As indicated, the above camera preferably has a focal plane array made of PtSi. However, the focal plane array can be of other materials and structures, e.g. indium antimonide (InSb), silicon-germanium, mercury cadmium telluride (HgCdTe), quantum well materials, pyroelectric materials, bolometers or thermopiles.

The above camera takes continuous wafer images and can be employed with film or without, e.g. as indicated in FIG. 2 hereof.

The method and apparatus of the invention can be used to image any material which is substantially transparent in the wavelength(s) of interest but which may contain defects or elemental compositions that absorb or scatter light at those wavelengths. If the material is transparent at these wavelengths, then the only data needed to perform, e.g. a quantitative EL2 defect measurement are the electron and hole photo-ionization cross-sections. Silicon, gallium arsenide and indium phosphide are examples of such materials as well as Germanium and other elements of Groups III & V of the Periodic Table of the Elements, alloys thereof, at least one film thereof deposited on a substrate, and multiple film layers thereof.

We claim:

1. A method for locating defects and non-uniformities in a solid material that is otherwise substantially transparent to infrared (IR) light comprising,
   a) placing an IR focal plane array camera before a source of IR radiation and spaced therefrom,
   b) placing said material between said camera and said source,
   c) activating said source to emit an IR beam that is transmitted through said material to said camera, said camera obtaining an image of said material and said defects without scanning,
   d) processing said image and
   e) outputting said image in a desired form.

2. The method of claim 1 wherein said IR beam is diffused to illuminate said material more uniformly.

3. The method of claim 1 wherein said material is in the form of a wafer.

4. The method of claim 3 wherein said wafer is a semiconductor selected from the group consisting of Si, GaAs, InP, Ge, other elements of Groups III and V of the Periodic Table of the Elements, alloys thereof, at least one film thereof deposited on a substrate and multiple film layers thereof.

5. The method of claim 1 wherein said image is converted to a digitized signal and such signal is fed to a computer for storage and analysis.

6. The method of claim 1 wherein the wavelength of said radiation is selected or varied en route to said camera for mapping or analysis purposes.

7. An apparatus for locating defects and non-uniformities in a solid material that is otherwise substantially transparent to infrared (IR) light comprising:
   a) a source of IR radiation,
   b) an IR focal plane array camera mounted before said source and spaced therefrom,
   c) means for placing said material between said camera and said source,
   d) means for activating said source to transmit an IR beam through said material to said camera, which obtains an image of said material and said defects without scanning,
   e) means for processing said image and
   f) means for outputting said image in a desired form.

8. The apparatus of claim 7, wherein an IR diffuser is mounted between said source and said material.

9. The apparatus of claim 7, wherein an IR wavelength or band selection device is mounted between said source and said material.

10. The apparatus of claim 9 wherein said device is an IR wavelength filter.

11. The apparatus of claim 7, wherein an IR wavelength or band selection device is mounted between said material and said camera.

12. The apparatus of claim 11 wherein said device is an IR wavelength filter.

13. The apparatus of claim 7 having a magnifying means mounted between said camera and said material for viewing a small area thereof.

14. The apparatus of claim 7 wherein said material is in the form of a wafer.

15. The apparatus of claim 7, wherein said means for outputting is a TV monitor.

16. The apparatus of claim 7 wherein said means for outputting is a frame-grabber for digitizing the camera's output image signal and means for feeding the digitized signal to a computer for storage and analysis thereof.

* * * * *